United States Patent [19]

Richardson et al.

[11] 4,257,774

[45] Mar. 24, 1981

[54] INTERCALATION INHIBITION ASSAY FOR COMPOUNDS THAT INTERACT WITH DNA OR RNA

[75] Inventors: Carol L. Richardson, Springfield; Gail E. Schulman, Alexandria, both of Va.

[73] Assignee: Meloy Laboratories, Inc., Springfield, Va.

[21] Appl. No.: 57,739

[22] Filed: Jul. 16, 1979

[51] Int. Cl.³ .................... C12Q 1/68; G01N 33/16; G01N 31/22
[52] U.S. Cl. .................................. 23/230 B; 435/6
[58] Field of Search ............................ 435/6, 7, 172; 23/230 B; 424/2, 7

[56] References Cited

PUBLICATIONS

Setnro, et al., "A Modified Method for the Determination of Microgram Quantities of DNA from Cell or Tissue Cultures", Anal. Biochem., vol. 71, No. 1, (1976) pp. 313-317.
Hill, "The Use of Anti-Tumor Antibiotics for Simple Quantitative Assays for DNA", Anal. Biochem., vol. 70, No. 2 (1976), pp. 635-638.
Kapuscinski, et al., "Simple and Rapid Fluorimetric Method for DNA Microassay", Anal. Biochem. vol. 83 No. 1 (1977), pp. 252-257.
Kubota, et al., "Fluoroescence Decay and Quantum Yield Charactistics of Acridine Orange and Proflavin Bound to DNA", Chem. Abstracts, vol. 87, No. 11 (1977), p. 178, Abs. No. 79901x.
Ellerton, et al., "The Interaction of DNA with Aminoacridines and Aminobenzacridines", Chem. Absts., vol. 89, No. 13 (1978), p. 281 Abs. No. 102140a.
Kischchenko, et al., "Relative Disposition of Stainable DNA Strands in DNP Fibers", Chem. Absts. vol. 89 No. 7 (1978) p. 184 Abs. No. 55058t.
Patel, et al. "Sequence Specificity of Mutagen-Nucleic Acid Complexes in Solution, Intercalation and Mutagen-base Pair Overlap Geomletries for Proflavine Binding to dC-dC-dG-dG and dG-dG-dG-dC Self-Complementary Duplexes", Chem. Abtracts, vol. 87 No. 15 (1977), p. 224, Abs. No. 113322w.
McMaster, et al., "Analysis of Single-and Double-Stranded Nucleic Acids on Polyacrylamide and Agarose Gels by Using Glycoxal and Acridine Orange" Chem. Absts. vol. 88, No. 3 (1978) p. 284, Abs. No. 18666y.

Primary Examiner—Thomas G. Wiseman
Attorney, Agent, or Firm—Leon E. Tenenbaum

[57] ABSTRACT

A novel method for the detection, screening, the quantitation of compounds that interact with nucleic acids (DNA or RNA) is provided. The basis for this method is the inhibition of acridine orange binding to the nucleic acid. Measurement of binding inhibition utilizes the rapid, repeatable technique of fluorescence polarization.

4 Claims, 3 Drawing Figures

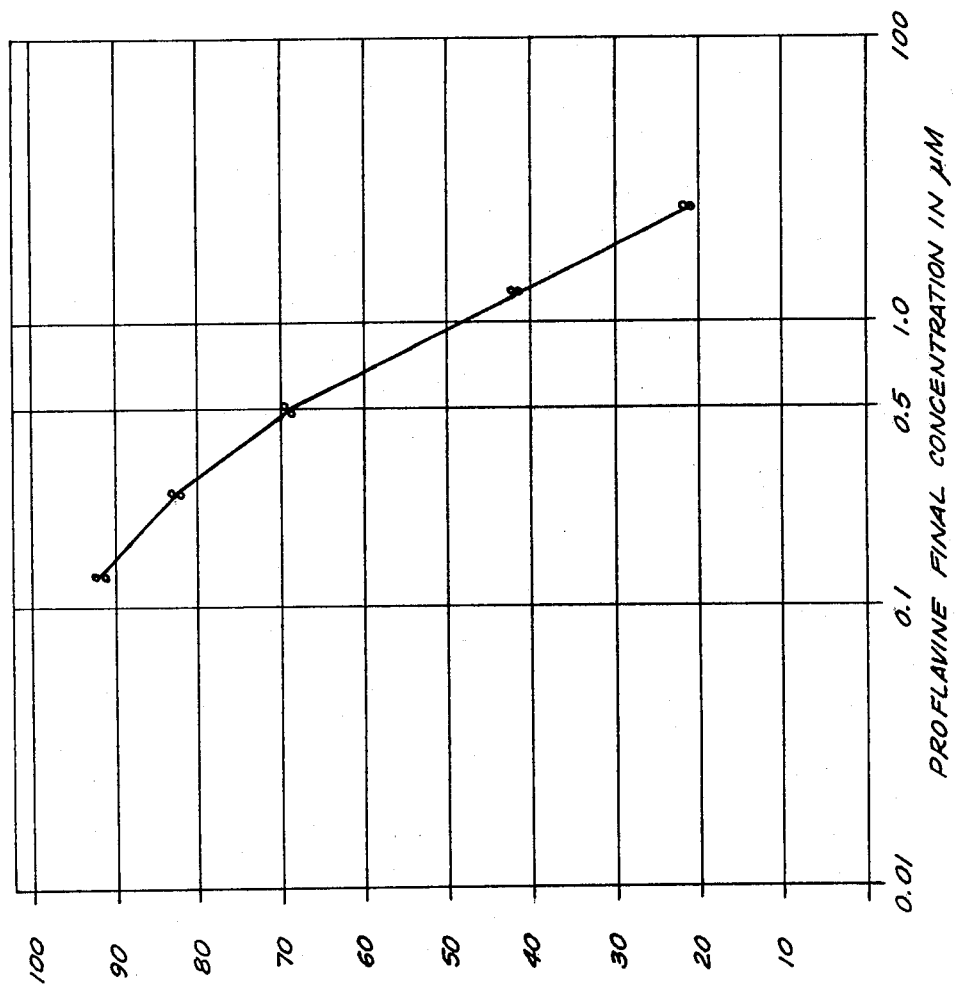

4,257,774

INTERCALATION INHIBITION ASSAY FOR COMPOUNDS THAT INTERACT WITH DNA OR RNA

FIELD OF THE INVENTION

DNA/RNA Binding Assays

DESCRIPTION OF THE PRIOR ART

The technique of fluorescence polarization is well-documented in the publications of Weber; "Fluorescence Techniques in Cell Biology", Springer Verlag, Berlin-Heidelberg-New York, 1973, pp. 5–13, and "Fluorescence and Phosphorescence Analysis", Interscience Publishers, New York-London-Sydney, 1966, pp. 217–240. This technique has been applied to measuring the interactions of antigens and antibodies, enzymes and substrates, membranes and ligands, and fluorescent cofactors and proteins. In addition, fluorescence polarization is used to study membrane microviscosities, activities of proteolytic enzymes and temperature and viscosity effects. Fluorescence polarization studies of the direct binding of several fluorescent intercalators to DNA has been reported (Plumbridge and Brown, Biochemica et Biophysica Acta, Vol. 479, 1977, pp. 441–449, Lerman, Proc. N.A.S., Vol. 49, 1963, pp. 94–101). These include ethidium, daunomycin, mepacrine, and acridine orange. However, the aim of these studies was to elucidate further the mode of binding of these compounds to DNA, and all of these studies involved the direct measurement of the fluorescent test compound itself. An additional report that relies upon the formation of a fluorescent complex upon binding of 4',6-diamidino-2-phenylindole to DNA is utilized to quantitate DNA. This is also a direct assay and is not dependent on the use of fluorescence polarization (Kapuscinski, J. and Skoczyles, B., Analytical Biochem., Vol. 83, 1977, pp. 252–257; Hill, B.T., Analytical Biochem. Vol. 70, 1976, pp. 635 ff.; and Setaro, F. and Morley, C.G.D., Analytical Biochem., Vol. 71, 1976, pp. 313 ff.).

A large percentage of compounds that bind to DNA are known to have mutagenic and/or carcinogenic activity and hence, it is of interest to have a rapid reproducible method for screening compounds that interact with DNA. In addition, a large number of antitumor drugs have as their mode of action binding to DNA; hence, this methodology may be applied to the screening of compounds for potential as antitumor drugs. A variety of techniques have been developed for studying the interaction of compounds with nucleic acids. These include equilibrium dialysis, analytical buoyant density centrifugation, nuclear magnetic resonance, inhibition of in vitro transcription, spectrophotometric analysis, circular dichroism, fluorescence quenching and melting temperature profiles. Of these methods, the rapid ones rely upon the intrinsic fluorescence of the test molecule itself, so with these methods a non-fluorescent molecule cannot be tested.

Other inherent disadvantages emerge when attempting to utilize the methods of the prior art for the simultaneous detection and quantitation of compounds which bind to nucleic acids. Many of the methods available for the assessment of DNA-binding by compounds require considerable time for measurement (i.e., analytical centrifugation, equilibrium dialysis, and melting temperature profiles). These methods preclude rapid quantification of the intercalator, and are generally employed qualitatively to ascertain if the compound interacts with DNA. Quantitative procedures that measure inhibition of DNA/RNA synthesis or induction of mutations as a function of the interaction of test compound with DNA involve far more complex systems and increase both the inherent variables and the time required for the assay. Other rapid quantitative methods, such as fluorescence quenching and spectrophotometric analysis, require that the compound in question be fluorescent. In addition, the sensitivity of these methods is limited by the difference in the relative fluorescence intensity or the magnitude of wavelength shifts upon chromophore binding to DNA.

OBJECTS OF THE INVENTION

Accordingly, it is an object of the present invention to provide a rapid procedure for the quantitative determination of compounds which bind with DNA or RNA.

It is another object of the present invention to provide a rapid procedure for the quantitative determination of compounds which bind with DNA or RNA, which compounds may or may not be fluorescent.

Other objects will appear from the description which follows.

SUMMARY OF THE INVENTION

It has been found that substances that interact with nucleic acids will compete with acridine orange for binding sites on DNA or RNA, or these substances will bind to the nucleic acid in such a way as to alter the DNA conformation, making acridine orange binding less favorable. Classic intercalators, such as ethidium bromide, actinomycin D, and proflavine, can be quantitated from standard curves. The maximum binding of acridine orange to the nucleic acids is measured by fluorescence polarization in an aqueous buffer system. By the addition of increasing concentrations of a biologically active test compound, the polarization value corresponding to maximum acridine orange binding is decreased. The amount of inhibition correlates directly with the concentration of the active test compound. Inactive test compounds do not decrease the maximum binding polarization of acridine orange, indicating they do not interact directly with nucleic acid.

What is unique in this process is that any test molecule whether or not fluorescent, that binds to DNA or RNA is detected by the displacement of a fluorescent intercalator, such as acridine orange. By using in the instrument excitation and emission filters which are specific for the particular intercalator being used, the fluorescence of the test compounds will not interfere.

DESCRIPTION OF THE PREFERRED EMBODIMENTS

In the preferred embodiments of the present invention, four solutions are required: (1) A solution of $10^{-5}$ M acridine orange prepared in 0.01 M cacodylate (or other suitable buffer); (2) Nucleic acid solution (approximately 10 $\mu$g/ml) in the same buffer. This reagent may be any of a variety of native DNAs (e.g., from calf thymus, *M. luteus,* or other organism), of synthetic DNA polymers, or RNAs; (3) A buffer system, used as the diluent; and (4) Test compound solution in buffer or dimethyl sulfoxide/dimethyl formamide.

The standard procedure is as follows: (1) 1.85 ml of buffer is added to a fluorimeter cuvette, then 100 $\mu$l of the acridine orange solution and 50 μl of test compound; (2) the initial fluorescence polarization value of freely rotating unbound acridine orange is determined in a fluorimeter equipped with a polarizer, which instrument is commercially available from a number of companies; (3) 50 μl of a nucleic acid solution of known concentration is added to the cuvette and mixed; and (4) the polarization value (P) is read again. This is repeated for a series of dilutions of the test compound, as well as a maximum binding control (with no test compound, only buffer). For each concentration of test compound, a percentage of maximum binding is determined. Compounds that are positive in the assay displace the acridine orange, and this is detected by a decrease in P value with increasing concentrations of test compound (i.e., a dose-response effect).

Fluorescent compounds other than acridine orange can be used if the instrument's excitation and emission wavelengths are adjusted to the optimum for these compounds. In the Fluoro I (Meloy Laboratories, Inc., Springfield, Va.), the excitation filter is 492 nm and the emission filter is 520 nm for acridine orange when doing DNA studies. The emission filter is changed to 650 for RNA binding studies. Acridine orange has been utilized most widely in our work because its excitation and emission wavelengths with DNA are the same as fluorescein (a compound that does not bind DNA); hence, allowing the use of fluorescein as a negative control. In addition, acridine orange binding to both DNA and RNA can be detected following excitation at 492 nm. However, binding to these substances can be differentiated by the emission wavelengths.

The method may be modified by: (1) changing the amounts of each component added to the cuvette; (2) introducing a preincubation step of the test compound with (a) the nucleic acid prior to addition of the acridine orange, or (b) chemically modifying enzymes or compounds, or (c) a combination of (a) and (b); (3) utilizing a variety of synthetic or natural nucleic acid solutions; or (4) using different intercalators.

The method will be more clearly understood from the following examples taken in conjunction with the drawings. In these drawings:

FIG. 3 shows the concentration curve for the inhibition of acridine orange intercalation by proflavine with *M. luteus* DNA.

EXAMPLE I

Figure 1:
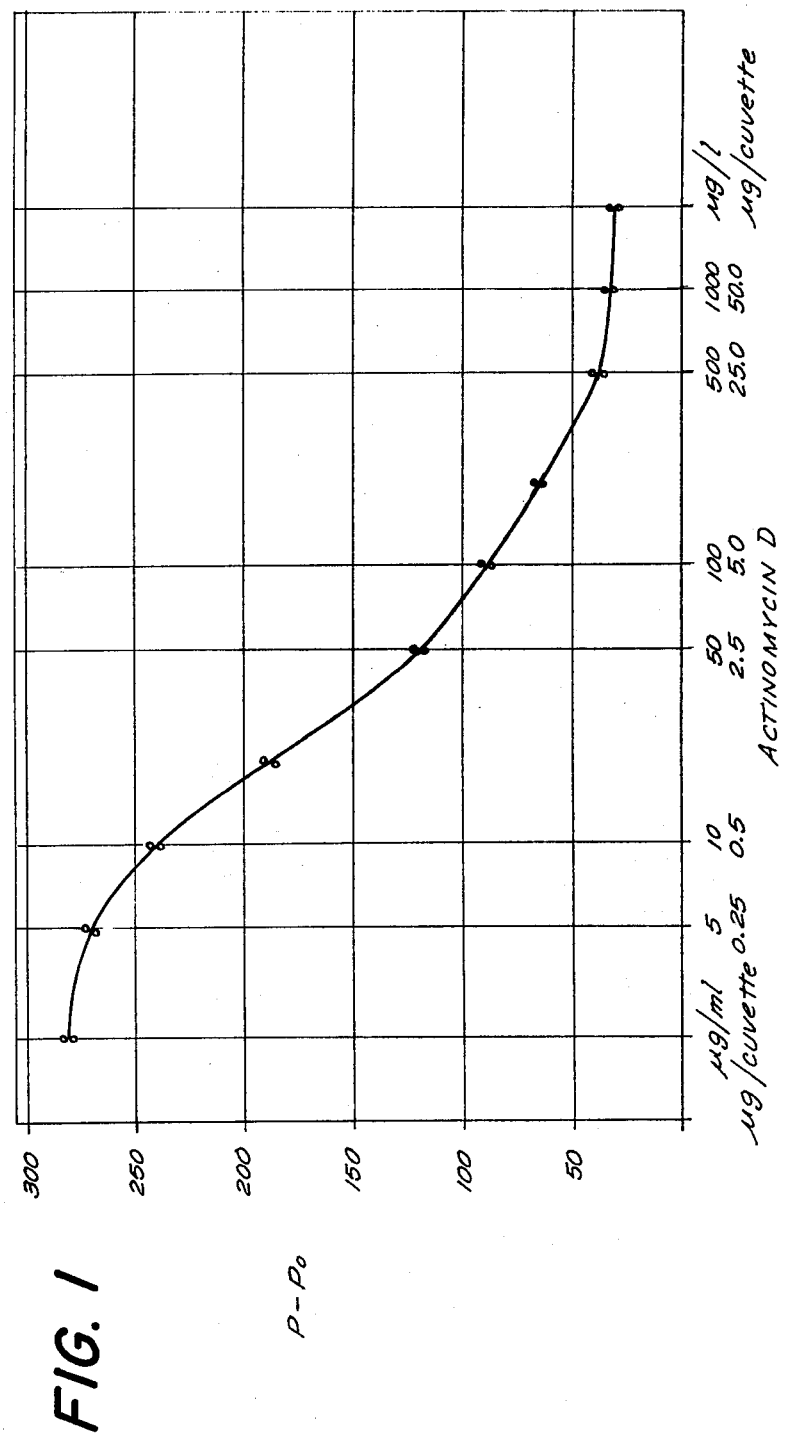
FIG. 1 shows the polarization value (P-$P_o$) vs. log of actinomycin D concentration showing increasing inhibition of intercalation of acridine orange with calf thymus DNA. The P-$P_o$ values given are actual polarizations amplified by a factor of $2.3 \times 10^3$.

In a cuvette, 200 μl of $10^{-5}$ M acridine orange is added to 1.75 ml of 0.01 M sodium cacodylate buffer (pH 6.7), 50 μl of actinomycin D is added (in concentrations ranging from 2 mg/ml to 2 μg/ml). The initial fluorescence polarization (Po) is determined in a Fluoro I polarizing fluorimeter, with 492 nm excitation and 520 nm emission filters in place. Then 8 μl of calf thymus DNA (125 μg/ml) is added to the cuvette, the solution is mixed, and a second polarization (P) value is determined. This procedure is repeated for each of the actinomycin concentrations to be tested. The data may be expressed as P-Po vs. log of actinomycin D concentration (refer to FIG. 1). The P-Po for a sample with an unknown concentration of actinomycin D can be determined similarly and the P-Po used to determine the concentration from the standard curves (e.g., FIG. 1). Alternatively, the data may be expressed as a percentage of maximum binding (i.e., when no actinomycin is added to the cuvette).

EXAMPLE II

The assay is performed as described in Example I, except that alternate sources of DNA are utilized, for example, *M. luteus* or poly dAdT. Because actinomycin D binds preferentially to cytosine and guanine residues, no inhibition is observed with poly dAdT with this test compound.

EXAMPLE III

The assay is performed as described in Example I, except RNA is used instead of DNA, and the emission filter is changed from 520 to 650 nm.

EXAMPLE IV

Figure 2:
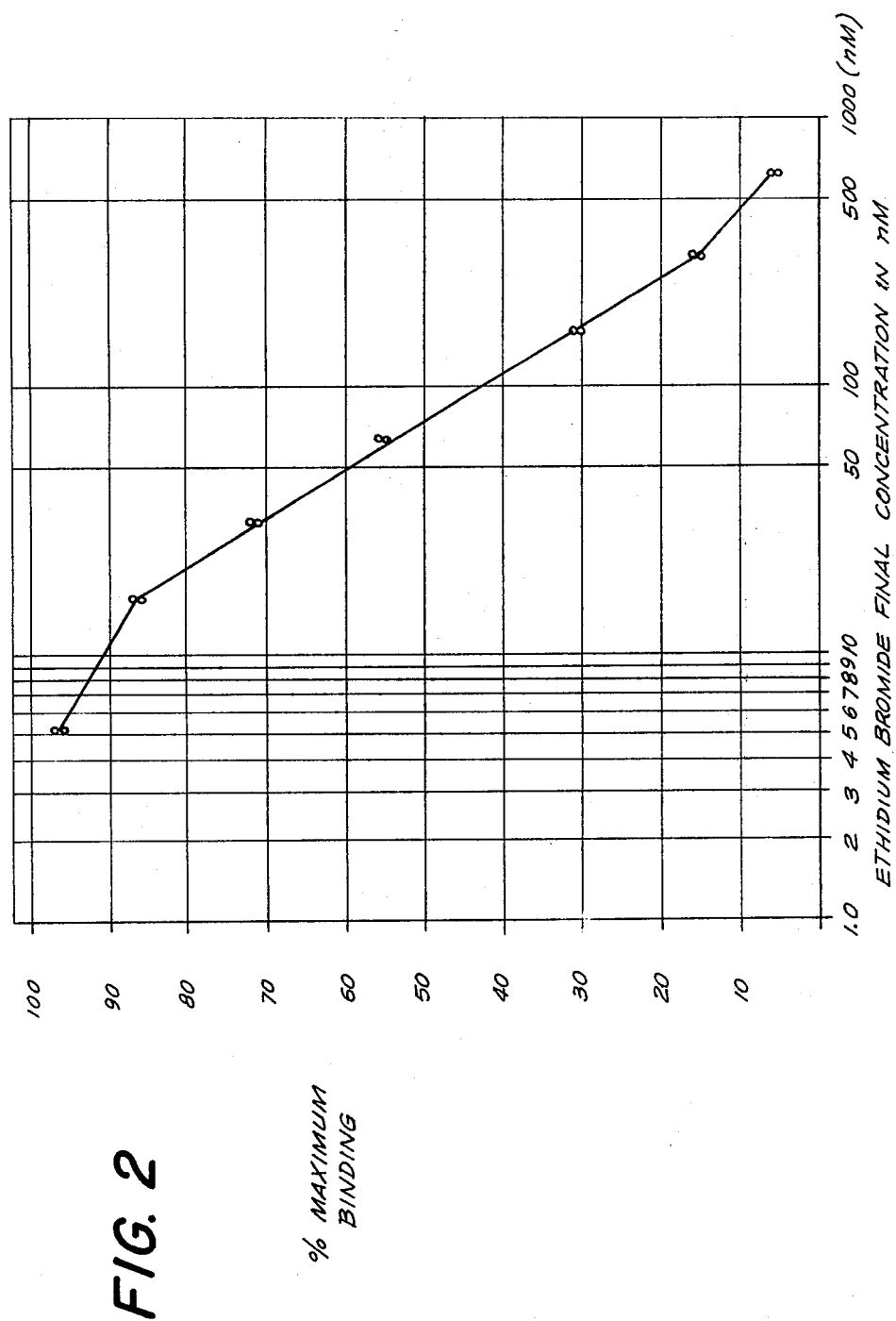
FIG. 2 shows the concentration curve for the inhibition of acridine orange intercalation by ethidium bromide with *M. luteus* DNA.

The assay is performed as described, except another agent that is known to or suspected of interacting with DNA or RNA is substituted for actinomycin D. FIGS. 2 and 3 show the results of two such compounds, ethidium bromide and proflavine.

EXAMPLE V

For compounds that interact weakly with nucleic acids, a pre-incubation of 10 mins. to 48 hrs. is incorporated into the procedure as follows. The buffer (1.5 to 1.8 ml), the DNA or RNA solution (5 to 100 μl) and the test compound (50 to 200 μl) are mixed in the cuvette and allowed to react for 10 mins. to 48 hrs. Then acridine orange is added to give a final concentration of 0.5 μM in 2 ml. Following mixing, the fluorescence polarization value is determined. Comparisons are made with controls (e.g., without potential inhibitor, and Po, without DNA or RNA).

The method of the present invention is of particular use in the study of the interactions of compounds with various classes of natural and synthetic nucleotides to determine the preferential binding of a given compound to certain nucleotide sequences, and in the screening of compounds for DNA binding activity for the determination of potential mutagenic activity of said compounds.

We claim:
1. A process for the quantitative determination of the extent of binding of a compound to a nucleic acid, which comprises the steps:
  (a) preparing a mixture containing said compound and an intercalator, said intercalator being selected from the group consisting of ethidium bromide, actinomycin D, proflavin and acridine orange, and determining the fluorescent polarization of said mixture;
  (b) adding the mixture of the compound and the intercalator to a nucleic acid under conditions suitable for the binding of both the compound and the intercalator to the nucleic acid, and determining the fluorescent polarization of the mixture containing the compound, the intercalator and the nucleic acid; and
  (c) determining the extent of binding of the compound to the nucleic acid from the difference in the fluorescent polarization of the mixture containing the compound and the intercalator and the mixture containing compound, the intercalator and the nucleic acid.

2. A process according to claim 1 wherein the nucleic acid is a natural or synthetic nucleic acid.

3. A process according to claim 2 wherein the nucleic acid is DNA or RNA.

4. A process according to claim 3 wherein the intercalator is acridine orange.

* * * * *